US011826200B2

(12) United States Patent
Choi et al.

(10) Patent No.: US 11,826,200 B2
(45) Date of Patent: Nov. 28, 2023

(54) MULTI-PLANE AND MULTI-MODE VISUALIZATION OF AN AREA OF INTEREST DURING AIMING OF AN ULTRASOUND PROBE

(71) Applicant: Verathon Inc., Bothell, WA (US)

(72) Inventors: Joon Hwan Choi, Bothell, WA (US); Fuxing Yang, Bothell, WA (US)

(73) Assignee: Verathon Inc., Bothell, WA (US)

( * ) Notice: Subject to any disclaimer, the term of this patent is extended or adjusted under 35 U.S.C. 154(b) by 509 days.

(21) Appl. No.: 16/150,518

(22) Filed: Oct. 3, 2018

(65) Prior Publication Data

US 2019/0099160 A1 Apr. 4, 2019

Related U.S. Application Data

(60) Provisional application No. 62/567,962, filed on Oct. 4, 2017.

(51) Int. Cl.
*A61B 8/00* (2006.01)
*A61B 8/08* (2006.01)
(Continued)

(52) U.S. Cl.
CPC .............. *A61B 8/467* (2013.01); *A61B 8/463* (2013.01); *A61B 8/466* (2013.01); *A61B 8/483* (2013.01);
(Continued)

(58) Field of Classification Search
CPC ....... A61B 8/467; A61B 8/4494; A61B 8/469; A61B 8/463; A61B 8/488; A61B 8/486;
(Continued)

(56) References Cited

U.S. PATENT DOCUMENTS 4,926,871 A 5/1990 Ganguly et al.
5,235,985 A * 8/1993 McMorrow .......... A61B 8/4494
600/443

(Continued)

FOREIGN PATENT DOCUMENTS

AU 2003 268 593 A1 1/2004
CN 1882850 A 12/2006
(Continued)

OTHER PUBLICATIONS

PCT International Search Report and Written Opinion issued for corresponding application No. PCT/US2018/054108 dated Feb. 11, 2019, 11 pages.

*Primary Examiner* — Jason M Ip
(74) *Attorney, Agent, or Firm* — Snyder, Clark, Lesch & Chung, LLP

(57) ABSTRACT

A system may include an ultrasound probe and a controller unit configured to communicate with the ultrasound probe. The controller unit may be further configured to select an aiming mode for the ultrasound probe; select a first aiming mode plane, scanning mode, or imaging mode; select at least one additional aiming mode plane, scanning mode, or imaging mode; toggle between obtaining and displaying ultrasound images associated with the first aiming mode plane, scanning mode, or imaging mode and obtaining and displaying ultrasound images associated with the at least one additional aiming mode plane, scanning mode, or imaging mode; receive a selection of a three-dimensional (3D) scan mode; and perform a 3D scan using the ultrasound probe, in response to receiving the selection of the 3D scan mode.

20 Claims, 13 Drawing Sheets

(51) Int. Cl.
*G01S 7/52* (2006.01)
*G01S 15/89* (2006.01)

(52) U.S. Cl.
CPC .......... *A61B 8/5207* (2013.01); *G01S 7/5208* (2013.01); *G01S 7/52057* (2013.01); *G01S 7/52085* (2013.01); *G01S 15/8911* (2013.01); *G01S 15/8915* (2013.01); *G01S 15/8938* (2013.01); *G01S 15/8993* (2013.01); *A61B 8/4488* (2013.01); *G01S 7/52074* (2013.01)

(58) Field of Classification Search
CPC .......... A61B 8/466; A61B 8/54; A61B 8/483; A61B 8/4466; A61B 8/5207; A61B 8/446; B06B 1/0644; B06B 1/0607; G01N 29/221; G01N 29/2406; G01N 29/04; G01N 29/2437; G01N 29/226; G01N 29/02; G01S 7/521; G01S 7/5208; G01S 7/52085; G01S 15/8993
See application file for complete search history.

(56) References Cited

U.S. PATENT DOCUMENTS

| | | |
|---|---|---|
| 5,454,371 A | 10/1995 | Fenster et al. |
| 5,709,206 A | 1/1998 | Teboul |
| 6,245,017 B1 | 6/2001 | Hashimoto et al. |
| 6,567,688 B1 | 5/2003 | Wang |
| 6,585,649 B1 | 7/2003 | Mendlein et al. |
| 7,744,534 B2 | 6/2010 | Chalana et al. |
| 7,841,984 B2 | 11/2010 | Cribbs et al. |
| 8,121,666 B2 | 2/2012 | Otsuka et al. |
| 8,308,643 B2 | 11/2012 | van der Steen et al. |
| 8,313,437 B1 | 11/2012 | Suri |
| 8,332,166 B2 | 12/2012 | Vanderby et al. |
| 8,419,641 B2 | 4/2013 | Chono |
| 8,506,487 B2 | 8/2013 | Masuzawa |
| 8,602,994 B2 | 12/2013 | Zheng et al. |
| 8,652,047 B2 | 2/2014 | Kim et al. |
| 8,657,751 B2 | 2/2014 | Tanabe |
| 8,672,846 B2 | 3/2014 | Napolitano et al. |
| 8,852,103 B2 | 10/2014 | Rothberg et al. |
| 8,926,513 B2 | 1/2015 | Yao et al. |
| 8,956,297 B2 | 2/2015 | Sumi |
| 9,364,196 B2 | 6/2016 | El-Aklouk et al. |
| 2003/0055338 A1* | 3/2003 | Steininger ............ G10K 11/355 600/459 |
| 2004/0267123 A1* | 12/2004 | McMorrow ............ A61B 5/204 600/443 |
| 2006/0235301 A1* | 10/2006 | Chalana ................. G06K 9/32 600/443 |
| 2006/0241482 A1 | 10/2006 | Karasawa |
| 2007/0088213 A1* | 4/2007 | Poland .................. G10K 11/34 600/437 |
| 2007/0197913 A1 | 8/2007 | Kim et al. |
| 2008/0249414 A1 | 10/2008 | Yang et al. |
| 2009/0030326 A1* | 1/2009 | Kim ....................... A61B 8/483 600/459 |
| 2009/0264757 A1 | 10/2009 | Yang et al. |
| 2010/0262007 A1 | 10/2010 | Medlin et al. |
| 2010/0286521 A1 | 11/2010 | Betts |
| 2011/0054296 A1 | 6/2011 | Kim et al. |
| 2011/0137172 A1 | 6/2011 | Kim et al. |
| 2011/0166451 A1 | 7/2011 | Blaivas et al. |
| 2011/0230766 A1 | 9/2011 | Medlin |
| 2011/0230768 A1 | 9/2011 | Nir et al. |
| 2012/0053467 A1 | 3/2012 | Betts |
| 2012/0302884 A1 | 11/2012 | Sandstrom et al. |
| 2014/0024937 A1 | 1/2014 | Kim et al. |
| 2017/0238907 A1 | 8/2017 | Kommu |

FOREIGN PATENT DOCUMENTS

| | | |
|---|---|---|
| CN | 101355905 A | 1/2009 |
| CN | 106073826 A | 11/2016 |
| JP | H03215252 A | 9/1991 |
| JP | H07204202 A | 8/1995 |
| JP | H10502194 A | 2/1998 |
| JP | 2000135217 A | 5/2000 |
| JP | 2001046377 A | 2/2001 |
| JP | 2003334198 A | 11/2003 |
| JP | 2003334198 A * | 11/2003 |
| JP | 2007000439 A | 1/2007 |
| JP | 2007082649 A | 4/2007 |
| JP | 2009022414 A | 2/2009 |
| JP | 2010194259 A | 9/2010 |
| JP | 2011530352 A | 12/2011 |
| JP | 201255765 A | 3/2012 |
| JP | 2014140410 A | 8/2014 |
| WO | WO-2007032682 A1 * | 3/2007 ............... A61B 8/12 |

* cited by examiner

MULTI-PLANE AND MULTI-MODE VISUALIZATION OF AN AREA OF INTEREST DURING AIMING OF AN ULTRASOUND PROBE

PRIORITY INFORMATION

This patent application claims benefit of priority to U.S. Provisional Application No. 62/567,962, entitled "MULTI-PLANE VISUALIZATION OF AN AREA OF INTEREST DURING AIMING OF AN ULTRASOUND PROBE" and filed on Oct. 4, 2017, which is hereby incorporated herein by reference in its entirety.

BACKGROUND INFORMATION

An ultrasound probe may generate ultrasound signals using a transducer, such as, for example, a piezoelectric transducer or a capacitive transducer, which converts electrical signals into ultrasound energy and which converts ultrasound echoes back into electrical signals. Ultrasound probes are typically used to identify a target organ or other structures in the body and/or determine features associated with the target organ/structure, such as the size of the organ/structure or the volume of fluid in the organ. In order for a user to properly scan a target organ/structure, the user may need to place the ultrasound probe in a particular position with respect to the target organ/structure. Correct placement of the ultrasound probe may present various challenges.

DETAILED DESCRIPTION OF PREFERRED EMBODIMENTS

Figure 1A:
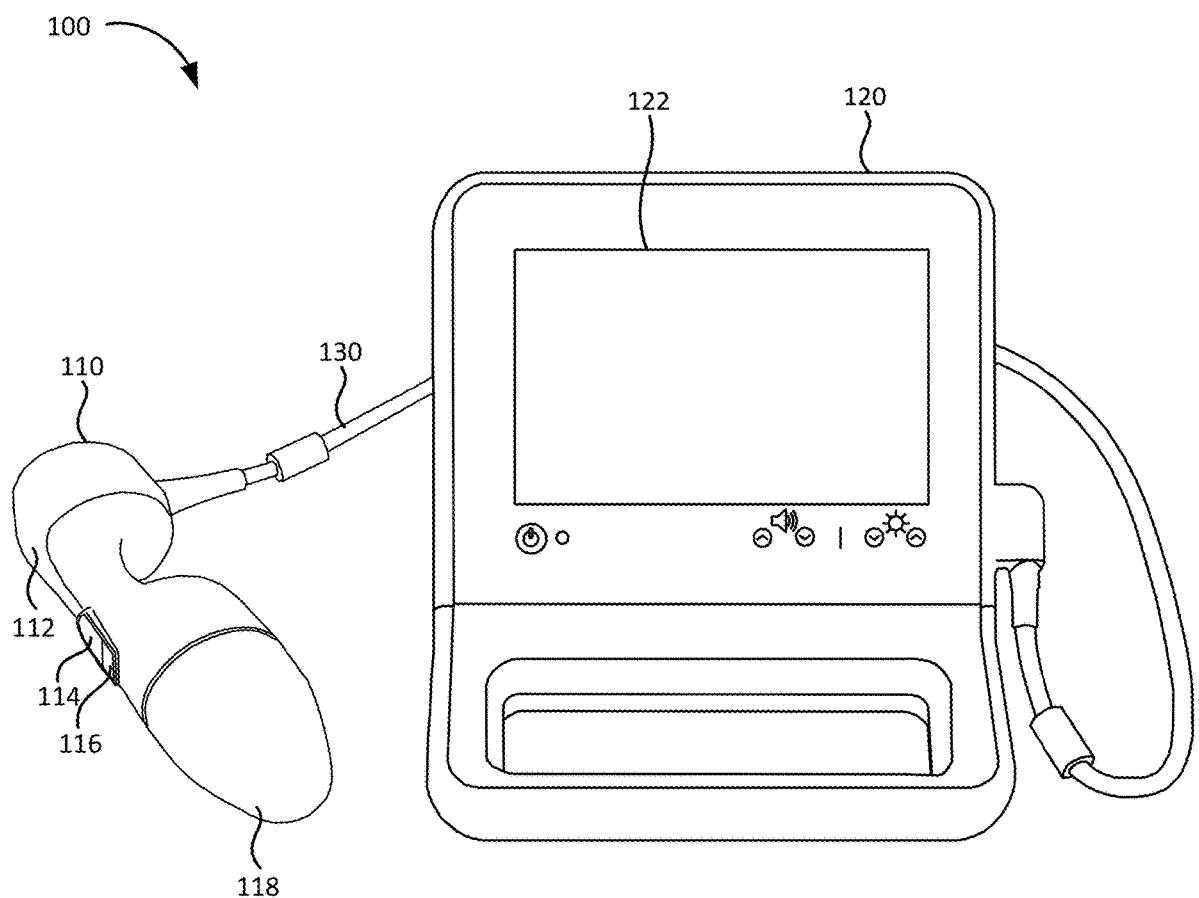
FIG. 1A is a diagram illustrating an exemplary ultrasound system according to an implementation described herein.

The following detailed description refers to the accompanying drawings. The same reference numbers in different drawings identify the same or similar elements.

An ultrasound probe may be positioned on a patient's body to perform a three-dimensional (3D) scan of an area of interest, such as a body organ, joint, blood vessel, and/or another type of area of a patient's body. A 3D scan may include a set of B-mode images captured in different planes transecting the area of interest. For example, a 3D scan may include B-mode images taken at particular angle intervals in a circle around a center of the area of interest.

Before the 3D scan is taken, the ultrasound probe may need to be accurately positioned over the area of interest. In order to position the ultrasound probe, a user may select an aiming mode for the ultrasound probe. During the aiming mode, the ultrasound probe may repeatedly perform a B-mode scan in a particular plane to display a cross-section of the area of interest in the particular plane. Thus, the user may use the B-mode scan image from the aiming mode to move the ultrasound probe around and align the ultrasound probe to an estimated center of the area of interest. However, in many situations, an area of interest may have cross-sections that significantly differ in size in different planes. Thus, a single B-mode plane may not be sufficient to position the ultrasound probe (e.g., to locate a target organ to be scanned) within the desired 3D volume and clipping of the area of interest may occur during the 3D scan. In other words, parts of the area of interest may be left out of the 3D scan, wasting time and resources.

Implementations described herein relate to multi-plane visualization of an area of interest during aiming of an ultrasound probe. An ultrasound system may be configured to select an aiming mode for an ultrasound probe, selecting a first aiming mode plane, and select at least one additional aiming mode plane without a user having to change the position of the ultrasound probe. The ultrasound system may then toggle between obtaining and displaying ultrasound images associated with the first aiming mode plane and obtaining and displaying ultrasound images associated with at least one additional aiming mode plane using the ultrasound probe until selection of a 3D scan mode is made. When the ultrasound system receives selection of the 3D scan mode, the ultrasound system may perform the 3D scan using the ultrasound probe. Use of multiple planes during an aiming mode may save time associated with the user attempting to position the ultrasound probe with respect to the area of interest.

In some implementations, the ultrasound images generated while in aiming mode and/or during a 3D scan may correspond to B-mode ultrasound images. In other implementations, other types of ultrasound images may be used during the aiming mode and the aiming mode may be followed by other types of images additionally or alternatively to a 3D scan. As an example, after selection of aiming mode planes, the ultrasound system may toggle between obtaining and displaying probability mode (P-mode) ultrasound images. A P-mode ultrasound image may correspond to an ultrasound image (e.g., a B-mode ultrasound image, etc.) in which each particular pixel is mapped to a probability indicating whether that particular pixel is within or part of a target organ/structure. As another example, the ultrasound system may toggle between obtaining and displaying segmentation map ultrasound images. A segmentation map ultrasound image may correspond to an ultrasound image with segmentation processing performed on captured ultrasound data. For example, in a segmentation map ultrasound image, different body structures may be displayed in different colors (e.g., bladder in yellow, background tissues in gray, etc.). As yet another example, after selection of aiming mode planes, the ultrasound system may toggle between obtaining and displaying Doppler mode ultrasound images (e.g., Power Doppler, Continuous Wave Doppler, Pulsed Wave Doppler, etc.), harmonic mode ultrasound images, motion mode (M-mode) ultrasound images, and/or any other type of imaging modality that uses ultrasound data. Moreover, the 3D scan may be performed using P-mode ultrasound images, Doppler mode ultrasound images, harmonic mode ultrasound images, M-mode ultrasound images, and/or any other type of imaging modality that uses ultrasound data.

The toggling, associated with the aiming modes, may include toggling between two orthogonal ultrasound imaging planes (e.g., a sagittal plane and a transverse plane), sequentially rotating between at least three different ultrasound imaging planes (e.g., planes separated by 60 degrees), or sequentially rotating between a different number of ultrasound imaging planes separated by particular angles. In some implementations, the multiple aiming mode planes may be displayed substantially simultaneously in real-time or near real-time (e.g., as each plane is scanned). In other implementations, a user may switch between the different scanning mode planes. For example, the ultrasound system may display a particular aiming mode plane, may detect activation of a toggle switch or input, and may switch to displaying another one of the aiming mode planes.

Furthermore, the toggling may include toggling between scanning modes. For example, rather than toggling between two or more imaging planes, a user may select to toggle between two or more scanning modes. A scanning mode may include a single plane scan, a bi-plane scan, a tri-plane scan, a quad-plane scan, and/or a scan that includes another number of planes. As an example, a user may select to toggle between a single plane scan and a bi-plane scan. Thus, the ultrasound system may scan a single scan plane and then may toggle to a bi-plane scan and scan two planes (e.g., two orthogonal planes). As another example, the user may select to toggle between a bi-plane scan and a tri-plane scan in which the ultrasound system toggles between scanning two planes and scanning three planes.

Moreover, the toggling may include toggling between imaging modes. For example, rather than toggling between two or more imaging planes, a user may select to toggle between two or more imaging modes. An imaging mode may include a B-mode ultrasound image scan, a Doppler mode ultrasound image (e.g., Power Doppler, Continuous Wave Doppler, Pulsed Wave Doppler, etc.) scan, a harmonic mode ultrasound image scan, a motion mode (M-mode) ultrasound image scan, a probability mode (P-mode) ultrasound image scan, a segmentation map ultrasound image scan, and/or another type of imaging mode scan. As an example, a user may select to toggle between a B-mode imaging mode and a Doppler mode imaging mode. As another example, a user may toggle between a P-mode imaging mode and a segmentation map imaging mode.

Furthermore, the toggling between different planes, scanning modes, and/or imaging modes may be performed mechanically and/or electronically. For example, in some implementations, the ultrasound probe may include a single element ultrasound transducer, a vertical motor to move the single element ultrasound transducer into different ultrasound imaging planes, and a horizontal motor to move the single element ultrasound transducer along a sector of a particular ultrasound imaging plane. Toggling between the aiming mode planes may include controlling the vertical motor to move a single element ultrasound transducer between different ultrasound imaging planes. In other implementations, the ultrasound probe may include an array of ultrasound transducers and a vertical motor to move the array of ultrasound transducers into different ultrasound imaging planes. Toggling between the aiming mode planes may include controlling the vertical motor to move the array of ultrasound transducers between different ultrasound imaging planes. In yet other implementations, the ultrasound probe may include a two-dimensional (2D) array of ultrasound transducers and toggling between the aiming mode planes may include controlling the 2D array of ultrasound transducers to generate ultrasound images in different ultrasound imaging planes.

Moreover, the toggling may be performed manually or automatically. As an example, a user may view a first scanning plane, scanning mode, and/or imaging mode and may toggle to a second scanning plane, scanning mode, and/or imaging mode by activating a toggle switch or a toggle selection object on a touch screen, voicing a toggling command, and/or otherwise causing the ultrasound system to toggle to the second scanning plane, scanning mode, and/or imaging mode. As another example, the user may select automatic toggling and the ultrasound system may automatically toggle between the first scanning plane, scanning mode, and/or imaging mode and the second scanning plane, scanning mode, and/or imaging mode (and/or additional scanning planes, scanning modes, or imaging modes) at a particular interval and/or rate. The particular interval and/or rate may be configurable by the user.

In some implementations, the aiming mode may be followed by other types of processing additionally or alternatively to a 3D scan. As an example, after selection of aiming mode planes, toggling between obtaining and displaying ultrasound images for the selected aiming mode planes, scanning modes, and/or imaging modes may be used in connection with positioning a needle guide for needle insertion (e.g., to obtain a biopsy sample, etc.). As another example, after selection of aiming mode planes, scanning modes, and/or imaging modes, toggling between obtaining and displaying ultrasound images for the selected aiming mode planes, scanning modes, and/or imaging modes may be used to measure the volume of an area of interest (e.g., bladder volume measurement, prostate volume measurement, uterus volume measurement, aorta size measurement, etc.). For example, two perpendicular aiming mode planes may be used to measure the volume of the area of interest.

FIG. 1A is a diagram illustrating an exemplary ultrasound system 100 according to an implementation described herein. As shown in FIG. 1A, ultrasound system 100 may include an ultrasound probe 110, a base unit 120, and a cable 130.

Ultrasound probe 110 may house one or more ultrasound transducers configured to generate ultrasound energy at a particular frequency and/or pulse repetition rate and to receive reflected ultrasound energy (e.g., ultrasound echoes) and convert the reflected ultrasound energy into electrical signals. For example, in some implementations, ultrasound probe 110 may be configured to transmit ultrasound signals in a range that extends from approximately about two megahertz (MHz) to approximately 10 or more MHz (e.g., 18 MHz). In other implementations, ultrasound probe 110 may be configured to transmit ultrasound signals in a different range. Furthermore, ultrasound probe 110 may house one or more motors for controlling the movement of the ultrasound transducer.

Ultrasound probe 110 may include a handle 112, a trigger 114, and a dome 118 (also referred to as a "nose"). A user (e.g., a medical practitioner, etc.) may hold ultrasound probe 110 via handle 112 and press trigger 114 to activate one or more ultrasound transceivers and transducers located in dome 118 to transmit ultrasound signals toward a patient's area of interest (e.g., a particular body organ, a body joint, a blood vessel, etc.). For example, probe 110 may be positioned on a pelvic area of a patient and over the patient's bladder.

Handle 112 enables a user to move probe 110 relative to a patient's area of interest. Activation of trigger 114 initiates an ultrasound scan of a selected anatomical portion while dome 118 is in contact with a surface portion of a patient's body when the patient's area of interest is scanned. In some implementations, trigger 114 may include a toggle switch 116. Toggle switch 116 may be used to toggle between different aiming planes, between different scanning modes, between different imaging mode, etc. during an aiming mode of ultrasound system 100. In other implementations, trigger 114 may not include a separate toggle switch 116 and trigger 114 may be used to toggle between different aiming planes, scanning modes, and/or imaging modes. In yet other implementations, toggle switch 116 may be located in a different location of ultrasound probe 110, and/or may be located on base unit 120. In yet other implementations, a toggling function may be executed via a touchscreen button on the display of base unit 120 and/or via another type of control, such as a microphone (e.g., via spoken commands).

Dome 118 may enclose one or more ultrasound transducers and may be formed from a material that provides an appropriate acoustical impedance match to the anatomical portion and/or permits ultrasound energy to be properly focused as it is projected into the anatomical portion. Dome 118 may also include transceiver circuitry that includes a transmitter and a receiver to transmit and receive ultrasound signals. Probe 110 may communicate with base unit 120 via a wired connection, such as via cable 130. In other implementations, probe 110 may communicate with base unit 120 via a wireless connection (e.g., Bluetooth, WiFi, etc.).

Base unit 120 may house and include one or more processors or processing logic configured to process reflected ultrasound energy that is received by probe 110 to produce an image of the scanned anatomical region. Furthermore, base unit 120 may include display 122 to enable a user to view images from an ultrasound scan, and/or to enable operational interaction with respect to the user during operation of probe 110. For example, display 122 may include an output display/screen, such as a liquid crystal display (LCD), light emitting diode (LED) based display, touchscreen, and/or another type of display that provides text and/or image data to a user.

For example, display 122 may provide instructions for positioning probe 110 relative to a selected anatomical portion of a patient. Alternatively, ultrasound probe 110 may include a small display (e.g., in handle 112) that provides instructions for positioning ultrasound probe 110. Display 122 may also display two-dimensional or three-dimensional images of the selected anatomical region. In some implementations, display 122 may include a graphical user interface (GUI) that allows the user to select various features associated with an ultrasound scan. For example, display 122 may include selection items (e.g., buttons, dropdown menu items, checkboxes, etc.) to select an aiming mode for probe 110 and/or to initiate a 3D scan after probe 110 has been successfully positioned with respect to the patient's area of interest. Furthermore, display 122 may include selection items to select particular types of ultrasound images to be obtained, such as B-mode images, P-mode images, segmentation map mode images, Doppler ultrasound images, harmonic mode images, M-mode images, and/or other types of ultrasound images. Moreover, display 122 may include selection items to select one or more aiming mode planes, scanning modes, and/or imaging modes. Additionally, display 122 may include a selection item to select whether to toggle manually or automatically between the selected aiming mode planes, scanning modes, and/or imaging modes.

Figure 1B:
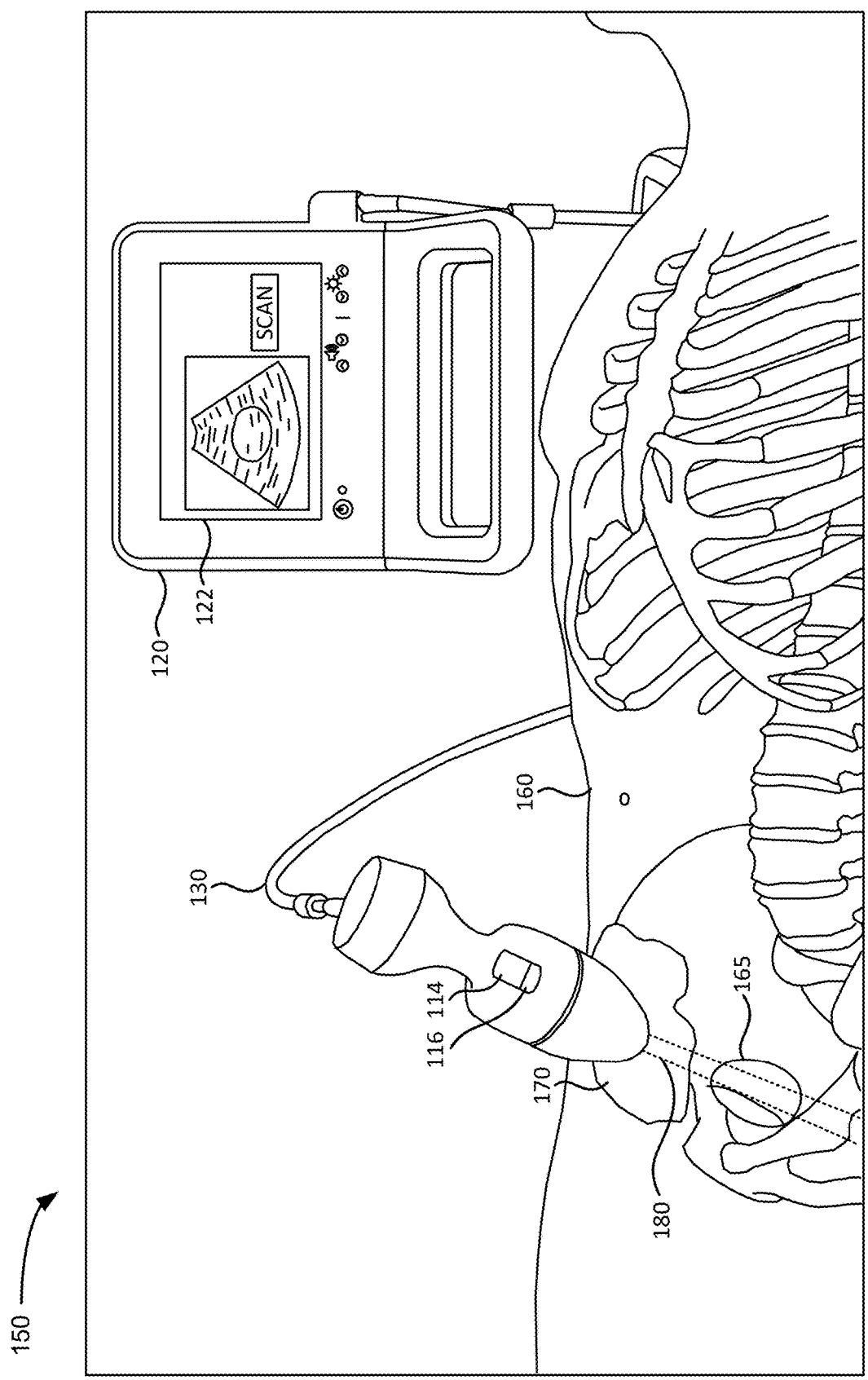
FIG. 1B is a diagram illustrating an exemplary environment for the ultrasound system of FIG. 1A according to an implementation described herein.

FIG. 1B is a diagram illustrating an exemplary environment 150 for ultrasound system 100 according to an implementation described herein. Environment 150 illustrates the operation of ultrasound system 100 with respect to a patient 160. As shown in FIG. 1B, patient 160 may be positioned so that a patient's area of interest may be scanned. For example, assume the area of interest corresponds to the patient's bladder 165. To scan bladder 165, ultrasound probe 110 may be positioned against a surface portion of patient 160 that is proximate to the anatomical portion to be scanned. The user may apply acoustic gel 170 (or gel pads) to the skin of patient 160 over the area of bladder 165 to provide an acoustical impedance match when dome 118 is placed against the skin.

The user may select an aiming mode via base unit 120 (e.g., by selecting an aiming mode button, menu item, etc., on display 122, by speaking a voice command, etc.). Alternatively, an aiming mode may be selected automatically when base unit 120 detects motion of ultrasound probe 110 or ultrasound probe 110 contacts acoustic gel 170 or the skin of patient 160 (e.g., via an accelerometer and/or gyroscope inside ultrasound probe 110). Ultrasound probe 110 may transmit ultrasound signals 180 through bladder 165 and may receive reflected ultrasound signals. The reflected ultrasound signals may be processed into images that are displayed on display 122.

In some implementations, the user may select one or more aiming mode planes, scanning modes, and/or imaging modes. In other implementations, one or more aiming mode planes, scanning modes, and/or imaging modes may be selected automatically without user input. In some implementations, display 122 may toggle between the selected aiming mode planes, scanning modes, and/or imaging modes automatically, without user input and/or without the user changing the position of ultrasound probe 110. In other implementations, the user may toggle between the selected aiming mode planes, scanning modes, and/or imaging modes using toggle switch 116. In yet other implementations, one or more of the selected aiming mode planes, scanning modes, and/or imaging modes may be displayed simultaneously on display 122. The user may adjust the position of ultrasound probe 110 based on the information displayed on display 122 until the user is satisfied that ultrasound probe 110 is positioned over bladder 165. The user may then activate a 3D scan of bladder 165 by pressing trigger 114, by pressing a scan button on display 122, by speaking a voice command, and/or using another type of scan activation technique.

Although FIGS. 1A and 1B show exemplary components of ultrasound system 100, in other implementations, ultrasound system 100 may include fewer components, different components, additional components, or differently arranged components than depicted in FIGS. 1A and 1B. Additionally or alternatively, one or more components of ultrasound system 100 may perform one or more tasks described as being performed by one or more other components of ultrasound system 100.

For example, in other embodiments, ultrasound probe 110 may correspond to a self-contained device that includes a microprocessor housed within ultrasound probe 110, configured to operably control the one or more ultrasound transducers, and to process the reflected ultrasound energy to generate ultrasound images. Accordingly, a display on ultrasound probe 110 may be used to display the generated images and/or to view other information associated with the operation of ultrasound probe 110. In yet other implementations, ultrasound probe 110 may be coupled to a general-purpose computer, such as a laptop, tablet, and/or a desktop computer (via a wired or wireless connection) that includes software that at least partially controls the operation of ultrasound probe 110 and/or that includes software to process information received from ultrasound probe 110 to generate ultrasound images.

Figure 2A:
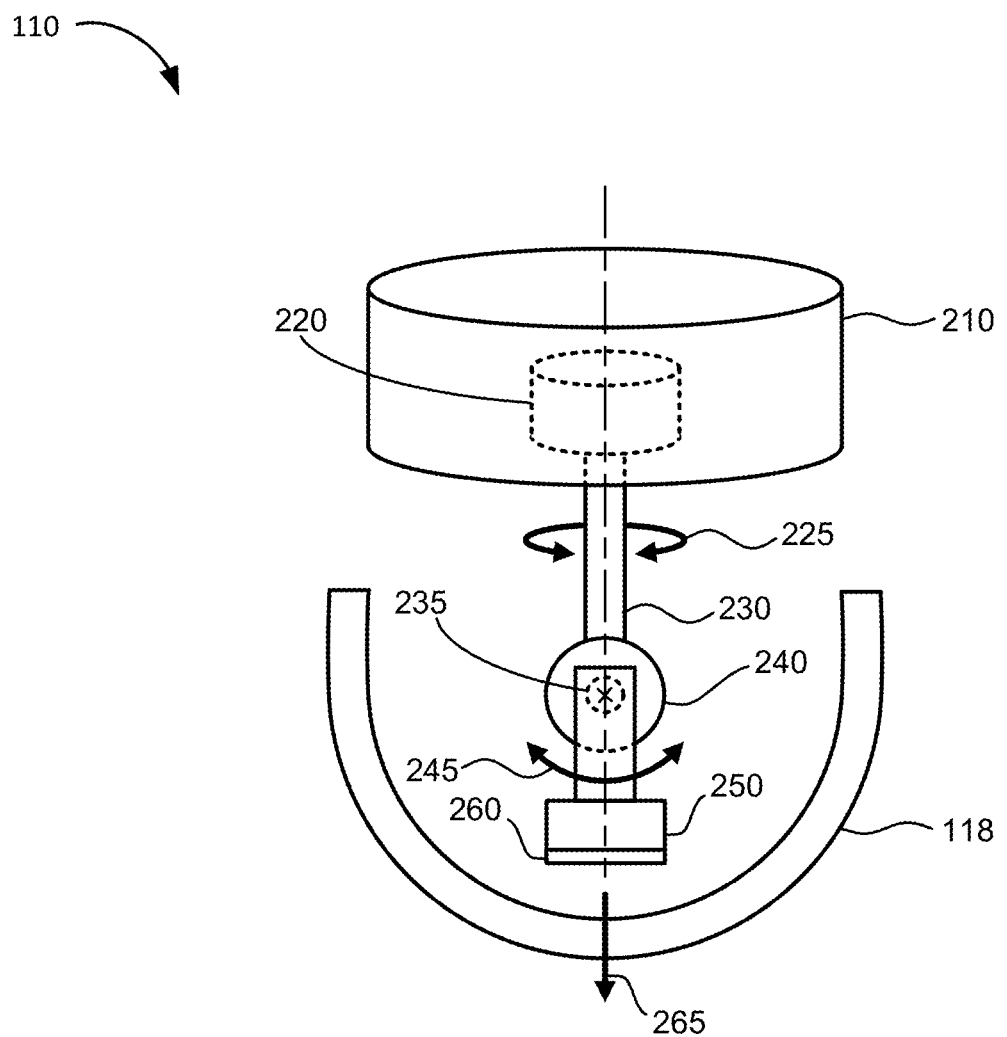
FIG. 2A is a diagram of a first exemplary ultrasound probe according to an implementation described herein.

FIG. 2A is a diagram of a first exemplary implementation of ultrasound probe 110 according to an implementation described herein. As shown in FIG. 2A, ultrasound probe 110 may include a single transducer element coupled to two rotational motors. In this implementation, ultrasound probe 110 may include a base 210 connected to dome 118, a theta motor 220, a spindle 230, a phi motor 240, and a transducer bucket 250 with a transducer 260. Theta motor 220, phi motor 240, and/or transducer 260 may include wired or wireless electrical connections that electrically connect theta motor 220, phi motor 240, and/or transducer 260 to base unit 120 via cable 130 (not shown in FIG. 2A).

Base 210 may house theta motor 220 and provide structural support to ultrasound probe 110. Base 210 may connect to dome 118 and may form a seal with dome 118 to protect the components of ultrasound probe 110 from the external environment. Theta motor 220 may rotate spindle 230 with respect to base 210 in a longitudinal direction with respect to transducer 260, by rotating around a vertical axis referred to herein as a theta (θ) rotational plane 225. Spindle 230 may terminate in a shaft 235 and phi motor 240 may be mounted onto shaft 235. Phi motor 240 may rotate around an axis orthogonal to the theta rotational plane 225 around a horizontal axis referred to herein as a phi (φ) rotational plane 245. Transducer bucket 250 may be mounted to phi motor 240 and may move with phi motor 240.

Transducer 260 may be mounted to transducer bucket 250. Transducer 260 may include a piezoelectric transducer, a capacitive transducer, and/or another type of ultrasound transducer. Transducer 260, along with transceiver circuitry associated with transducer 260, may convert electrical signals to ultrasound signals at a particular ultrasound frequency or range of ultrasound frequencies, may receive reflected ultrasound signals (e.g., echoes, etc.), and may convert the received ultrasound signals to electrical signals. Transducer 260 may transmit and receive ultrasound signals in a signal direction 265 that is substantially perpendicular to the surface of transducer 260.

Signal direction 265 may be controlled by the movement of phi motor 240 and the orientation of phi motor may be controlled by theta motor 220. For example, phi motor 240 may rotate back and forth across an angle that is less than 180 degrees to generate ultrasound image data for a particular plane and theta motor 220 may rotate to particular positions to obtain ultrasound image data for different planes.

In an aiming mode, theta motor 220 may remain stationary while phi motor 240 rotates back and forth to obtain ultrasound image data for a particular aiming plane. In the aiming mode, theta motor 220 may move back and forth between multiple aiming planes and phi motor 240 may rotate back and forth to obtain ultrasound image data. As an example, theta motor 220 may move back between two orthogonal planes while the aiming mode is selected. As another example, theta motor 220 may sequentially rotate through three planes at 120 degrees to each other during the aiming mode.

In a 3D scan mode, theta motor 220 may cycle through a set of planes one or more times to obtain a full 3D scan of an area of interest. In each particular plane of the set of planes, phi motor 240 may rotate to obtain B-mode image data for the particular plane. The movement of theta motor 220 and phi motor 240 may be interlaced in the 3D scan motor. For example, the movement of phi motor 240 in a first direction may be followed by a movement of theta motor 220 from a first plane to a second plane, followed by the movement of phi motor 240 in a second direction opposite to the first direction, followed by movement of theta motor 220 from the second plane to a third plane, etc. Such interlaced movement may enable ultrasound probe 110 to obtain smooth continuous volume scanning as well as improving the rate at which the scan data is obtained.

Figure 2B:
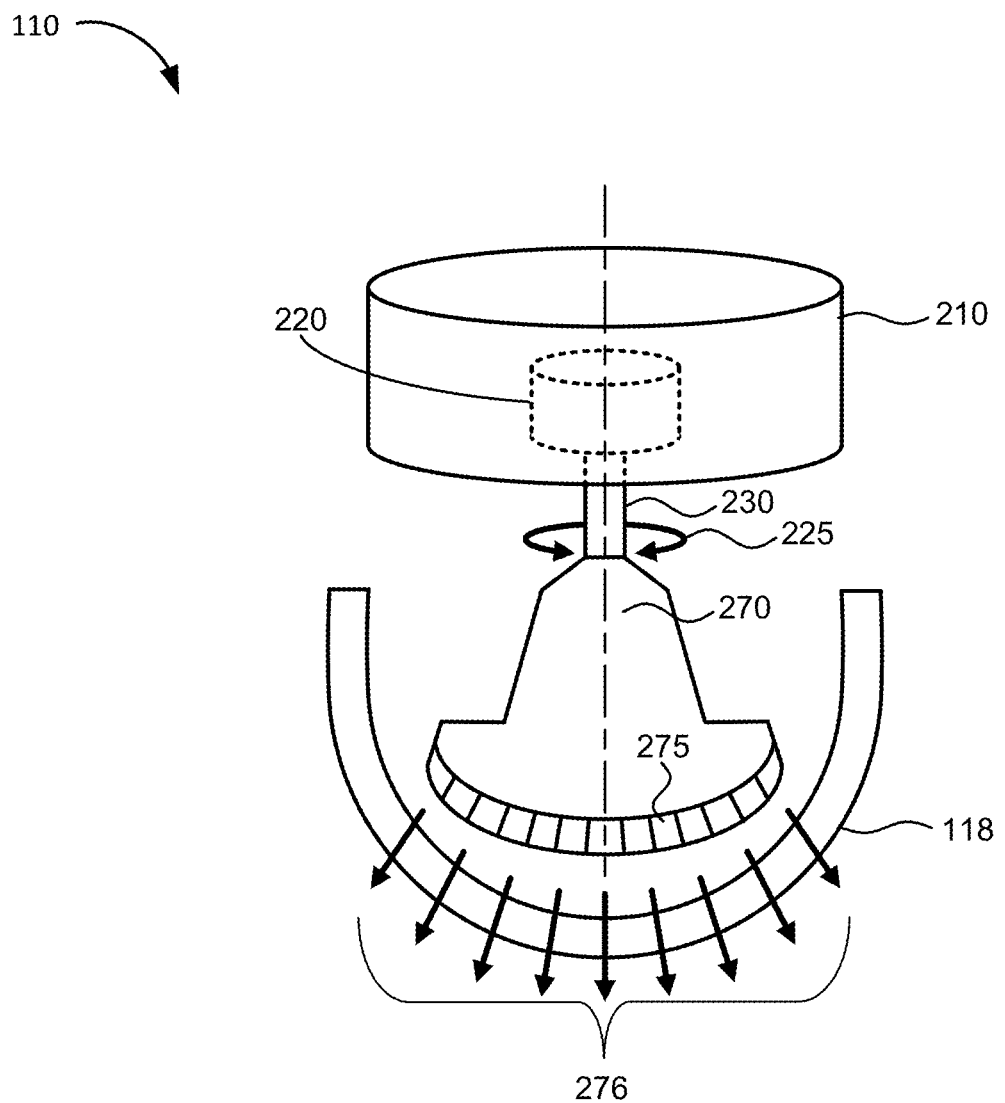
FIG. 2B is a diagram of a second exemplary ultrasound probe according to an implementation described herein.

FIG. 2B is a diagram of a second exemplary implementation of ultrasound probe 110 according to an implementation described herein. As shown in FIG. 2B, ultrasound probe 110 may include a one-dimensional (1D) array of transducer elements coupled to a rotation motor. In this implementation, ultrasound probe 110 may include a base 210 connected to dome 118, a theta motor 220, a spindle 230, and a transducer bucket 270 with a 1D transducer array 275. Theta motor 220 and/or 1D transducer array 275 may include wired or wireless electrical connections that electrically connect theta motor 220 and/or 1D transducer array 275 to base unit 120 via cable 130 (not shown in FIG. 2B).

Base 210 may house theta motor 220 and provide structural support to ultrasound probe 110. Base 210 may connect to dome 118 and may form a seal with dome 118 to protect the components of ultrasound probe 110 from the external environment. Theta motor 220 may rotate spindle 230 with respect to base 210 in longitudinal direction with respect to 1D transducer array 275 by rotating around theta rotational plane 225. Spindle 230 may terminate in transducer bucket 270. 1D transducer array 275 may be mounted to transducer bucket 270. 1D transducer array 275 may include a curved 1D array of piezoelectric transducers, capacitive transducers, and/or other types of ultrasound transducers. 1D transducer array 275 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 1D transducer array 275 may transmit and receive ultrasound signals in a particular direction of a set of directions, illustrated as item 276 in FIG. 2B. Thus, together, the elements of 1D transducer array 275 may generate ultrasound image data for a particular plane.

In an aiming mode, theta motor 220 may remain stationary while 1D transducer array 275 obtains ultrasound image data for a particular aiming plane. In the aiming mode, theta motor 220 may move back and forth between multiple aiming planes and 1D transducer array 275 may obtain ultrasound image data in each aiming plane. As an example, theta motor 220 may move back between two orthogonal planes while aiming mode is selected. As another example, theta motor 220 may sequentially rotate through three planes located 120 degrees apart from each other. In a 3D scan mode, theta motor 220 may cycle through a set of planes one or more times to obtain a full 3D scan of an area of interest. In each particular plane of the set of planes, 1D transducer array 275 may obtain ultrasound image data for the particular plane.

Figure 2C:
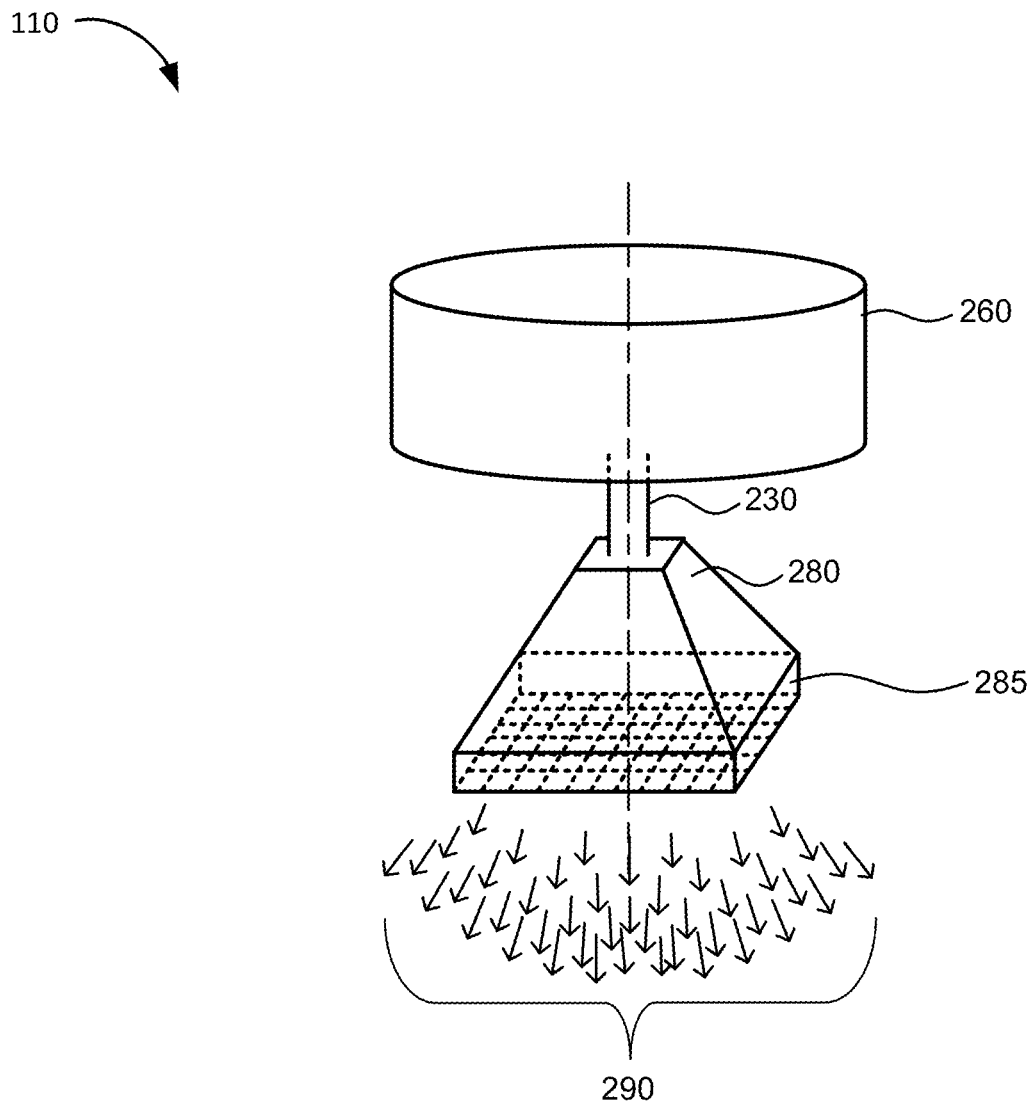
FIG. 2C is a diagram of a third exemplary ultrasound probe according to an implementation described herein.

FIG. 2C is a diagram of a third exemplary ultrasound probe 110 according to an implementation described herein. As shown in FIG. 2C, ultrasound probe 110 may include a two-dimensional (2D) array of transducer elements. In this implementation, ultrasound probe 110 may include a base 210, a spindle 230, and a transducer bucket 280 with a 2D transducer array 285. 2D transducer array 285 may include wired or wireless electrical connections that electrically connects 2D transducer array 285 to base unit 120 via cable 130 (not shown in FIG. 2C).

Base 210 may provide structural support to ultrasound probe 110 and secure spindle 230. Spindle 230 may terminate in transducer bucket 280. 2D transducer array 285 may be mounted to transducer bucket 280. 2D transducer array 285 may include a 2D array of piezoelectric transducers, capacitive transducers, and/or other types of ultrasound transducers. 2D transducer array 285 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 2D transducer array 285 may transmit and receive ultrasound signals in a particular direction of a set of directions, illustrated as item 290 in FIG. 2C. Thus, together, the elements of 2D transducer array 285 may generate ultrasound image data for multiple planes to generate a 3D ultrasound scan. In other words, 2D transducer array 285 may be controlled to tilt an ultrasound beam electronically in a particular direction.

In an aiming mode, 2D transducer array 285 may obtain ultrasound image data for one or more selected aiming planes. For a particular selected aiming plane, a linear 1D set of transducer elements from 2D transducer array 285 may be selected to generate an ultrasound image for the particular selected aiming plane. As an example, two 1D sets of transducers may be selected for two orthogonal planes and may alternate between obtaining ultrasound images of the two orthogonal planes. Alternatively, the ultrasound images for the two orthogonal planes may be obtained substantially simultaneously. As another example, 2D transducer array 285 may cycle through three planes located 120 degrees apart from each other and three sets of 1D sets of transducer elements from 2D transducer array 285 may obtain the ultrasound images for the three planes. In a 3D scan mode, 2D transducer array 285 may cycle through sets of 1D sets of transducer elements one or more times to obtain a full 3D scan of an area of interest. Alternatively, multiple sets of 1D sets of transducer elements, or even all of the transducer elements, of 2D transducer array 285 may be activated substantially simultaneously to obtain a full 3D scan of the area of interest.

Although FIGS. 2A, 2B, and 2C show exemplary components of ultrasound probe 110, in other implementations, ultrasound probe 110 may include fewer components, different components, additional components, or differently arranged components than depicted in FIGS. 2A, 2B, and 2C. Additionally or alternatively, one or more components of ultrasound probe 110 may perform one or more tasks described as being performed by one or more other components of ultrasound probe 110.

Figure 3:
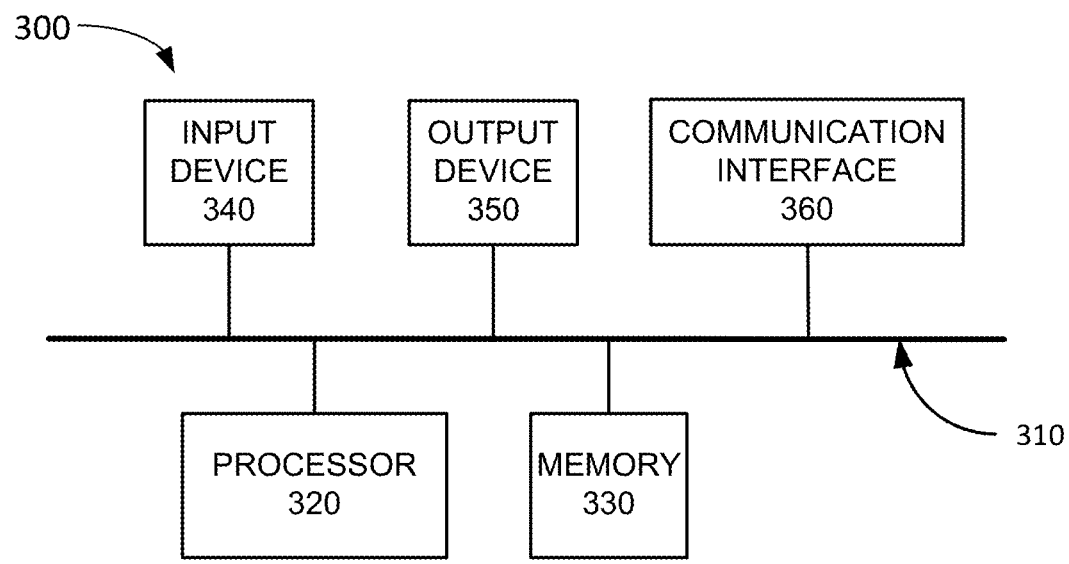
FIG. 3 is a diagram illustrating exemplary components of the controller unit of FIG. 1A.

FIG. 3 is a diagram illustrating example components of a device 300 according to an implementation described herein. Ultrasound probe 110 and/or base unit 120 may each include one or more devices 300. As shown in FIG. 3, device 300 may include a bus 310, a processor 320, a memory 330, an input device 340, an output device 350, and a communication interface 360.

Bus 310 may include a path that permits communication among the components of device 300. Processor 320 may include any type of single-core processor, multi-core processor, microprocessor, latch-based processor, and/or processing logic (or families of processors, microprocessors, and/or processing logics) that interprets and executes instructions. In other embodiments, processor 320 may include an application-specific integrated circuit (ASIC), a field-programmable gate array (FPGA), and/or another type of integrated circuit or processing logic.

Memory 330 may include any type of dynamic storage device that may store information and/or instructions, for execution by processor 320, and/or any type of non-volatile storage device that may store information for use by processor 320. For example, memory 330 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

Input device 340 may allow an operator to input information into device 300. Input device 340 may include, for example, a keyboard, a mouse, a pen, a microphone, a remote control, an audio capture device, an image and/or video capture device, a touch-screen display, and/or another type of input device. In some embodiments, device 300 may be managed remotely and may not include input device 340. In other words, device 300 may be "headless" and may not include a keyboard, for example.

Output device 350 may output information to an operator of device 300. Output device 350 may include a display, a printer, a speaker, and/or another type of output device. For example, device 300 may include a display, which may include a liquid-crystal display (LCD) for displaying content to the customer. In some embodiments, device 300 may be managed remotely and may not include output device 350. In other words, device 300 may be "headless" and may not include a display, for example.

Communication interface 360 may include a transceiver that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 360 may include a transmitter that converts baseband signals to radio frequency (RF) signals and/or a receiver that converts RF signals to baseband signals. Communication interface 360 may be coupled to an antenna for transmitting and receiving RF signals.

Communication interface 360 may include a logical component that includes input and/or output ports, input and/or output systems, and/or other input and output components that facilitate the transmission of data to other devices. For example, communication interface 360 may include a network interface card (e.g., Ethernet card) for wired communications and/or a wireless network interface (e.g., a WiFi) card for wireless communications. Communication interface 360 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

As will be described in detail below, device 300 may perform certain operations relating to multi-plane visualization of an area of interest during an aiming mode. Device 300 may perform these operations in response to processor 320 executing software instructions contained in a computer-readable medium, such as memory 330. A computer-readable medium may be defined as a non-transitory memory device. A memory device may be implemented within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of, or in combination with, software instructions to implement processes described herein. Thus, implementations described herein are not limited to any specific combination of hardware circuitry and software.

Although FIG. 3 shows exemplary components of device 300, in other implementations, device 300 may include fewer components, different components, additional components, or differently arranged components than depicted in FIG. 3. Additionally or alternatively, one or more components of device 300 may perform one or more tasks described as being performed by one or more other components of device 300.

Figure 4:
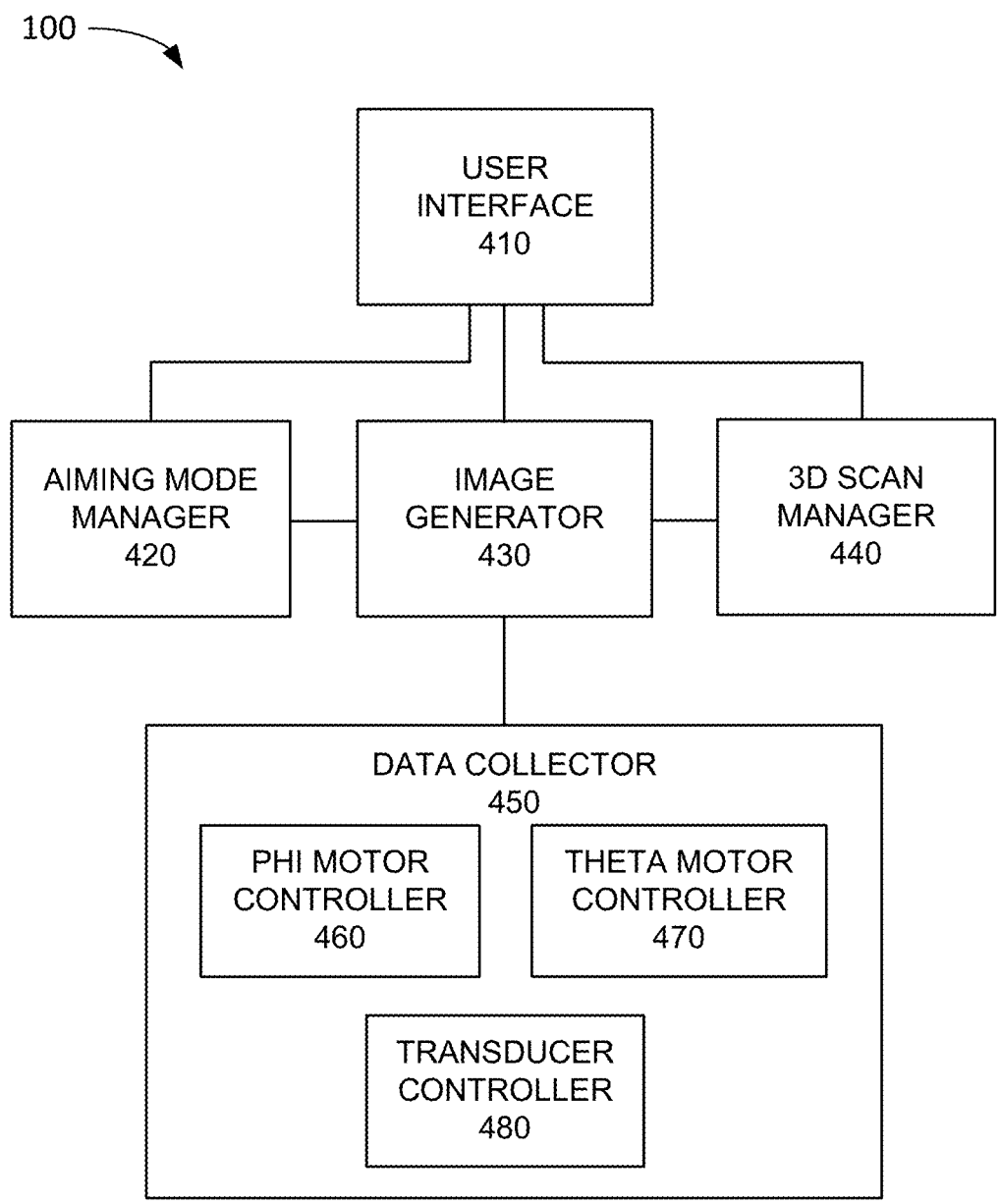
FIG. 4 is a diagram illustrating exemplary functional components of the system of FIG. 1A.

FIG. 4 is a diagram illustrating exemplary functional components of ultrasound system 100. The functional components of ultrasound system 100 may be implemented, for example, via processor 320 executing instructions from memory 330. Alternatively, some or all of the functional components of ultrasound system 100 may be implemented via hard-wired circuitry. As shown in FIG. 4, ultrasound system 100 may include a user interface 410, an aiming mode manager 420, an image generator 430, a 3D scan manager 440, and a data collector 450.

User interface 410 may generate a user interface (e.g., a graphical user interface) that displays ultrasound images to a user via display 122 and that is configured to receive selections and/or commands from the user via a touchscreen associated with display 122, via one or more control keys located on base unit 120 and/or on ultrasound probe 110, via a microphone included in base unit 120, and/or via another type of input method. For example, a user may select a type of ultrasound image, an aiming mode via user interface 410, may select one or more aiming mode planes, scanning modes, and/or imaging modes, and/or may select to perform a 3D scan once the user is satisfied with the position of ultrasound probe 110 during an aiming mode.

Aiming mode manager 420 may manage an aiming mode associated with ultrasound system 100. As an example, when a user selects to perform a scan, ultrasound system 100 may automatically enter an aiming mode. As another example, a user may select an aiming mode using a selection item and/or by executing a particular command. In some implementations, aiming mode manager 420 may select a default set of aiming mode planes, such as, for example, two orthogonal planes. Additionally or alternatively, a user may select one or more aiming mode planes, scanning modes, and/or imaging modes. As an example, a user may select a first aiming mode plane by specifying a particular plane (e.g., "sagittal," "frontal," etc.) and may select additional aiming mode planes by specifying each additional plane. As another example, a user may select a first scanning mode by specifying a first number of scanning planes and a second scanning mode by specifying a second number of scanning planes. As yet another example, a user may select a first imaging mode and a second imaging mode.

Aiming mode planes may be selected via a name, via an angle offset (e.g., second plane being first plane plus 90 degrees, etc.), by selecting an aiming mode plane set (e.g., two orthogonal planes, three planes separated by 60 degrees, four planes separated by 45 degrees, two planes separated by 45 degrees and a third plane orthogonal to a plane bisecting an angle between the two planes, etc.), by drawing or selecting each plane across a circle that is drawn around a graphical representation of the area of interest on the touchscreen of display 122, and/or by using another technique. Scanning modes may be selected by specifying the number of scanning planes for each selected scanning mode. Imaging modes may be selected from a list of available imaging modes.

Aiming mode manager 420 may instruct image generator 430 to generate ultrasound images for the selected aiming mode planes using particular types of ultrasound images, such as B-mode ultrasound images, P-mode ultrasound images, Doppler ultrasound images, segmentation map mode ultrasound images, harmonic mode ultrasound images, M-mode ultrasounds images, and/or other types of ultrasound images. In some implementations, aiming mode manager 420 may automatically toggle between the selected aiming mode planes, scanning modes, and/or imaging modes and may display ultrasound images associated with the selected aiming mode planes, scanning modes, and/or imaging modes on display 122. The ultrasound images associated with the different aiming mode planes, scanning modes, and/or imaging modes may be displayed simultaneously or display 122 may toggle through displaying the different aiming mode plane, scanning mode, and/or imaging mode images. In other implementations, the user may toggle between the different aiming mode plane, scanning mode, and/or imaging mode images by pressing toggle switch 116 and/or by otherwise selecting to toggle between the different aiming mode plane, scanning mode, and/or imaging mode images (e.g., by pressing a toggle button on the touchscreen of display 122, by speaking a command, etc.).

Image generator 430 may generate ultrasound images in particular planes. For example, image generator 430 may instruct data collector to obtain a particular type of ultrasound image, to move to a particular plane (e.g., a particular position of theta motor 220), and to generate an ultrasound image of a particular type for the particular plane (e.g., using phi motor 240 and transducer 260).

3D scan manager 440 may generate a 3D scan for an area of interest in a patient's body. For example, in response to a user selecting to perform the 3D scan, 3D scan manager 440 may instruct image generator 430 to generate ultrasound images for a particular set of planes in a particular sequence. In some implementations, the 3D scan may be implemented with an interlaced movement of theta motor 220 and phi motor 240. The number of planes that are scanned during a 3D scan (e.g., the number of different positions of theta motor 220) may be configurable by the user. For example, the 3D scan may be set to scan a plane every 30 degrees, every 15 degrees, every 10 degrees, every 5 degrees, etc.

Data collector 450 may be configured to collect ultrasound image data from ultrasound probe 110. Data collector 450 may include a phi motor controller 460, a theta motor controller 470, and a transducer controller 480. Phi motor controller 460 may control phi motor 240. Theta motor controller 470 may control theta motor 220. Transducer controller 480 may control transducer 260 (or 1D transducer array 275 or 2D transducer array 285).

Although FIG. 4 shows exemplary components of ultrasound system 100, in other implementations, ultrasound system 100 may include fewer components, different components, additional components, or differently arranged components than depicted in FIG. 4. Additionally or alternatively, one or more components of ultrasound system 100 may perform one or more tasks described as being performed by one or more other components of ultrasound system 100.

Figure 5:
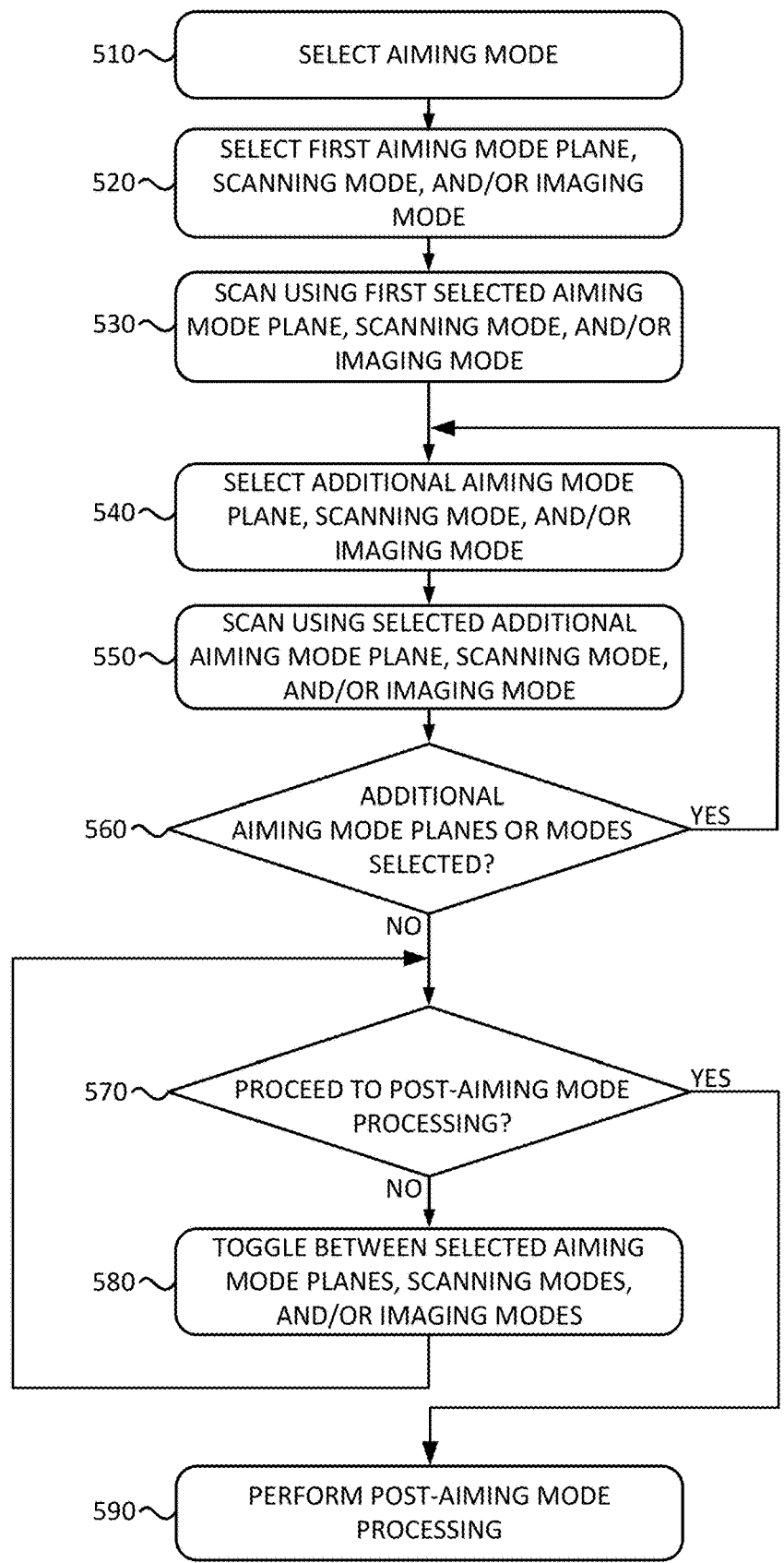
FIG. 5 is a flowchart of a process for multi-plane visualization during aiming according to an implementation described herein.

FIG. 5 is a flowchart of a process for multi-plane visualization during aiming according to an implementation described herein. In some implementations, the process of FIG. 5 may be performed by ultrasound system 100. In other implementations, some or all of the process of FIG. 5 may be performed by another device or a group of devices separate from ultrasound system 100.

The process of FIG. 5 may include selecting an aiming mode (block 510). As an example, when a user selects to perform a scan and/or turns on ultrasound system 100, ultrasound system 100 may automatically enter an aiming mode. As another example, a user may select an aiming mode using a selection item and/or by executing a particular command. Furthermore, a user may select a particular type of ultrasound image to use during the aiming mode. For example, the user may select to use B-mode ultrasound images, P-mode ultrasound images, Doppler ultrasound images, harmonic mode ultrasound images, M-mode ultrasound images, and/or other types of ultrasound images.

A first aiming mode plane, scanning mode, and/or imaging mode may be selected (block 520) and the first aiming mode plane, scanning mode, and/or imaging mode may be scanned (block 530). In some implementations, ultrasound system 100 may use a default plane (e.g., sagittal plane, transverse plane, etc.) as a first aiming mode plane, a default scanning mode (e.g., a single plane scan, etc.), and/or a default imaging mode (e.g., B-mode, etc.). In other implementations, a user may select a first aiming mode plane by selecting a plane from a list of planes, by specifying a name of the plane, by specifying an angle offset (e.g., from a sagittal plane), by drawing or selecting a line across an area of interest displayed on display 122, and/or by using another technique. Additionally or alternatively, the user may select a first scanning mode and/or imaging mode by selecting a scanning mode and/or imaging mode from a presented list of scanning modes and/or imaging modes. Ultrasound system 100 may scan and display the selected first aiming mode, scanning mode, and/or imaging mode in display 122.

An additional aiming mode plane, scanning mode, and/or imaging mode may be selected (block 540) and the selected additional aiming mode plane, scanning mode, and/or imaging mode may be scanned (block 550). For example, a user may select an additional aiming mode plane, scanning mode, and/or imaging mode using one or more of the techniques described above and ultrasound system 100 may scan and display the selected additional aiming mode, scanning mode, and/or imaging mode in display 122, without the user having to change the position of ultrasound probe 110. A determination may be made as to whether additional aiming mode planes, scanning modes, and/or imaging modes are selected (block 560). For example, ultrasound system 100 may continue to toggle between the selected aiming mode planes, scanning modes, and/or imaging modes, and the user may select another aiming mode plane, scanning mode, and/or imaging mode.

If it is determined that additional aiming mode planes, scanning modes, and/or imaging modes are selected (block 560—YES), processing may return to block 540. If it is determined that additional aiming mode planes, scanning modes, and/or imaging modes are not selected (block 560—NO), a determination may be made as to whether to proceed to post-aiming mode processing (block 570). As an example, ultrasound system 100 may determine that a selection has been made to perform a 3D scan. A 3D scan may be selected by, for example, selecting a 3D scan button on the touchscreen of display 122, by pressing a particular key on base unit 120 and/or ultrasound probe 110, by speaking a voice command, and/or using another technique. As another example, ultrasound system 100 may determine that a user has selected to position a needle guide by, for example, making a needle guide selection from a list of options provided on display 122. As yet another example, ultrasound system 100 may determine that a user has selected to analyze an area of interest (e.g., measure the volume of an organ, measure the amount of fluid in an organ, measure the blood flow through an area, etc.) by, for example, making an analysis mode selection from a list of options provided on display 122.

If it is determined that processing is not to proceed to post-aiming mode processing (block 570—NO), toggling between the selected aiming mode planes, scanning modes, and/or imaging modes may be performed (block 580). For example, ultrasound system 100 may continue to toggle between the selected aiming mode planes, scanning modes, and/or imaging modes until the 3D scan is selected and/or until a different mode is selected (e.g., ultrasound system 100 is placed in an idle mode, etc.). If it is determined that processing is to proceed to a 3D scan (block 570—YES), a post-aiming mode processing may be performed (block 590). As an example, after the user is satisfied with the alignment of ultrasound probe 110, based on the information displayed via multiple aiming mode planes during aiming mode, the user may select to perform the 3D scan and ultrasound system 100 may perform the 3D scan.

In some implementations, ultrasound system 100 may continue to toggle between the selected aiming mode planes, scanning modes, and/or imaging modes during post-aiming processing. As an example, the user may select a needle guide mode. In response, ultrasound system 100 may enter a needle guide mode that provides images and/or instructions to the user while the user operates the needle guide and while ultrasound system 100 continues to toggle between the selected aiming mode planes, scanning modes, and/or imaging modes.

As yet another example, ultrasound system 100 may determine that a user has selected to analyze an area of interest by selecting to measure the volume of an organ or body cavity, by selecting to measure the amount of fluid in an organ or body cavity, by selecting to measure blood flow through an area of interest, and/or by selecting another type of analysis. In response, ultrasound system 100 may enter an analysis mode and perform the requested measurement while ultrasound system 100 continues to toggle between the selected aiming mode planes, scanning modes, and/or imaging modes.

Figure 6:
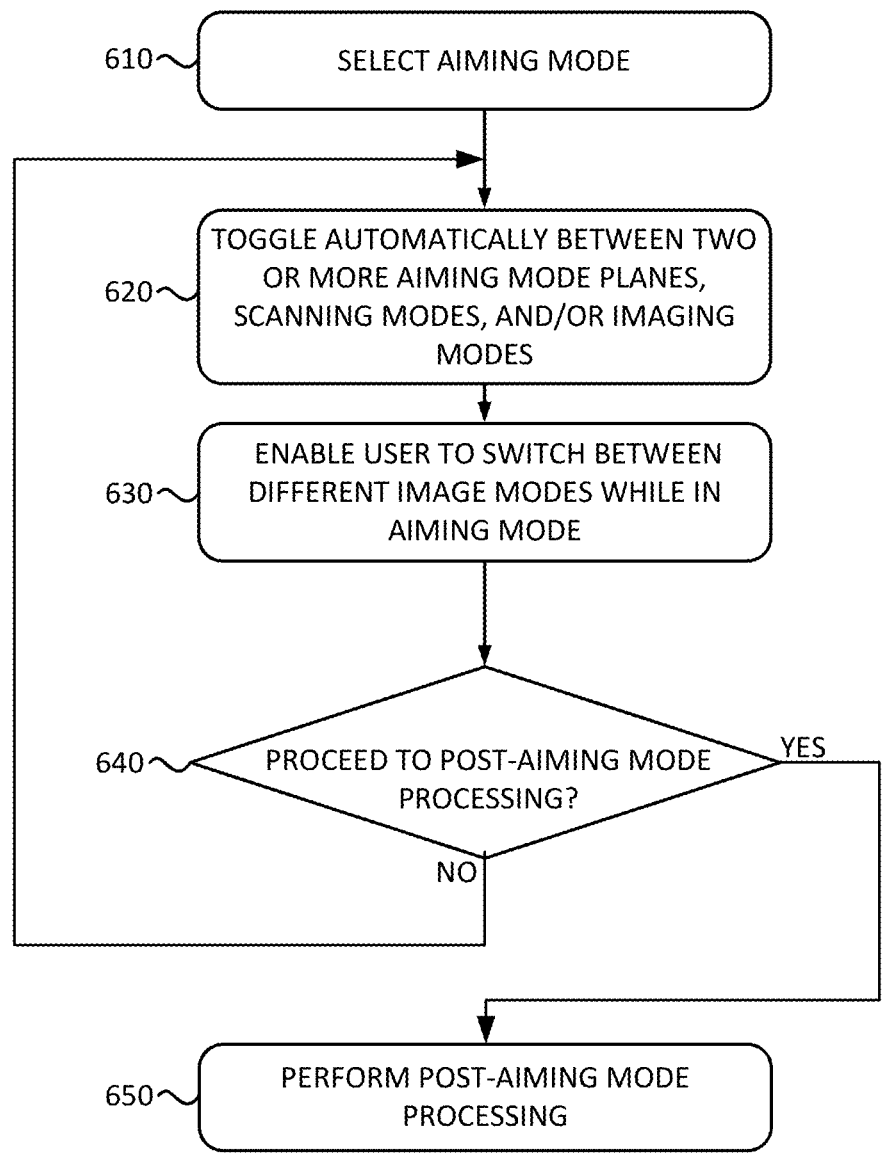
FIG. 6 is a flowchart of another process for multi-plane visualization during aiming according to an implementation described herein.

FIG. 6 is a flowchart of another process for multi-plane visualization during aiming according to an implementation described herein. In the process of FIG. 6, when ultrasound system 100 is activated, and/or when an aiming mode is selected, ultrasound system 100 may automatically toggle between two or more aiming mode planes, scanning modes, and/or imaging modes without requiring manual toggling. In some implementations, automatic toggling may be used as a default aiming mode and/or while a user operates a needle guide and/or another type of medical device inside a patient's body. In some implementations, the process of FIG. 6 may be performed by ultrasound system 100. In other implementations, some or all of the process of FIG. 6 may be performed by another device or a group of devices separate from ultrasound system 100.

The process of FIG. 6 may include selecting an aiming mode (block 610). As an example, when a user selects to perform a scan and/or turns on ultrasound system 100, ultrasound system 100 may automatically enter an aiming mode. As another example, a user may select a particular aiming mode using a selection item and/or by executing a particular command, such as by selecting a default aiming mode, a needle guide aiming mode, and/or another type of aiming mode.

Toggling between two or more aiming mode planes, scanning modes, and/or imaging modes may occur (block 620). For example, in response to the selected aiming mode, ultrasound system 100 may automatically toggle between a particular set of aiming mode planes, scanning modes, and/or imaging modes while ultrasound system 100 is in the selected aiming mode. As an example, ultrasound system 100 may toggle between two orthogonal planes, such as a sagittal plane and a transverse plane. As another example, ultrasound system 100 may sequentially rotate through three planes at 120 degrees to each other in response to the selected aiming mode. As yet another example, ultrasound system 100 may toggle between a single plane scan and a bi-plane scan. As yet another example, ultrasound system 100 may toggle between B-mode images and P-mode images. Ultrasound system 100 may toggle between the set of aiming mode planes, scanning modes, and/or imaging modes at a particular toggling rate. The user may be provided with a selection object and/or a voice command option to enable the user to increase or decrease the toggling rate.

The user may be enabled to switch between different image modes while in the aiming mode (block 630). For example, ultrasound system 100 may provide a selection object and/or a voice command option to enable to user to select a particular type of ultrasound image to use during the aiming mode, such as, for example, B-mode ultrasound images, P-mode ultrasound images, Doppler ultrasound images, harmonic mode ultrasound images, M-mode ultrasound images, and/or other types of ultrasound images. As an example, while trying to find a target vessel for needle insertion using automatic toggling between two orthogonal B-mode images, the user may select to turn Doppler on or off to find the target vessel more efficiently.

A determination may be made as to whether to proceed to post-aiming mode processing (block 640). As an example, ultrasound system 100 may determine that a selection has been made to perform a 3D scan. As another example, ultrasound system 100 may determine that the user has exited the aiming mode after, for example, performing a successful insertion of a needle into a target area, such as a blood vessel. As yet another example, ultrasound system 100 may determine that a user has selected to analyze an area of interest (e.g., measure the volume of an organ, measure the amount of fluid in an organ, measure the blood flow through an area, etc.) by, for example, making an analysis mode selection from a list of options provided on display 122.

If it is determined that processing is not to proceed to post-aiming mode processing (block 640—NO), automatic toggling between the two or more aiming mode planes, scanning modes, and/or imaging modes may continue to be performed (block 620). If it is determined that processing is to proceed to a 3D scan (block 640—YES), a post-aiming mode processing may be performed (block 650). As an example, after the user is satisfied with the alignment of ultrasound probe 110, based on the information displayed via the two or more aiming mode planes, scanning modes, and/or imaging modes during aiming mode, the user may select to perform the 3D scan and ultrasound system 100 may perform the 3D scan. As another example, ultrasound system 100 may exit the aiming mode without performing any additional processing.

Figure 7:
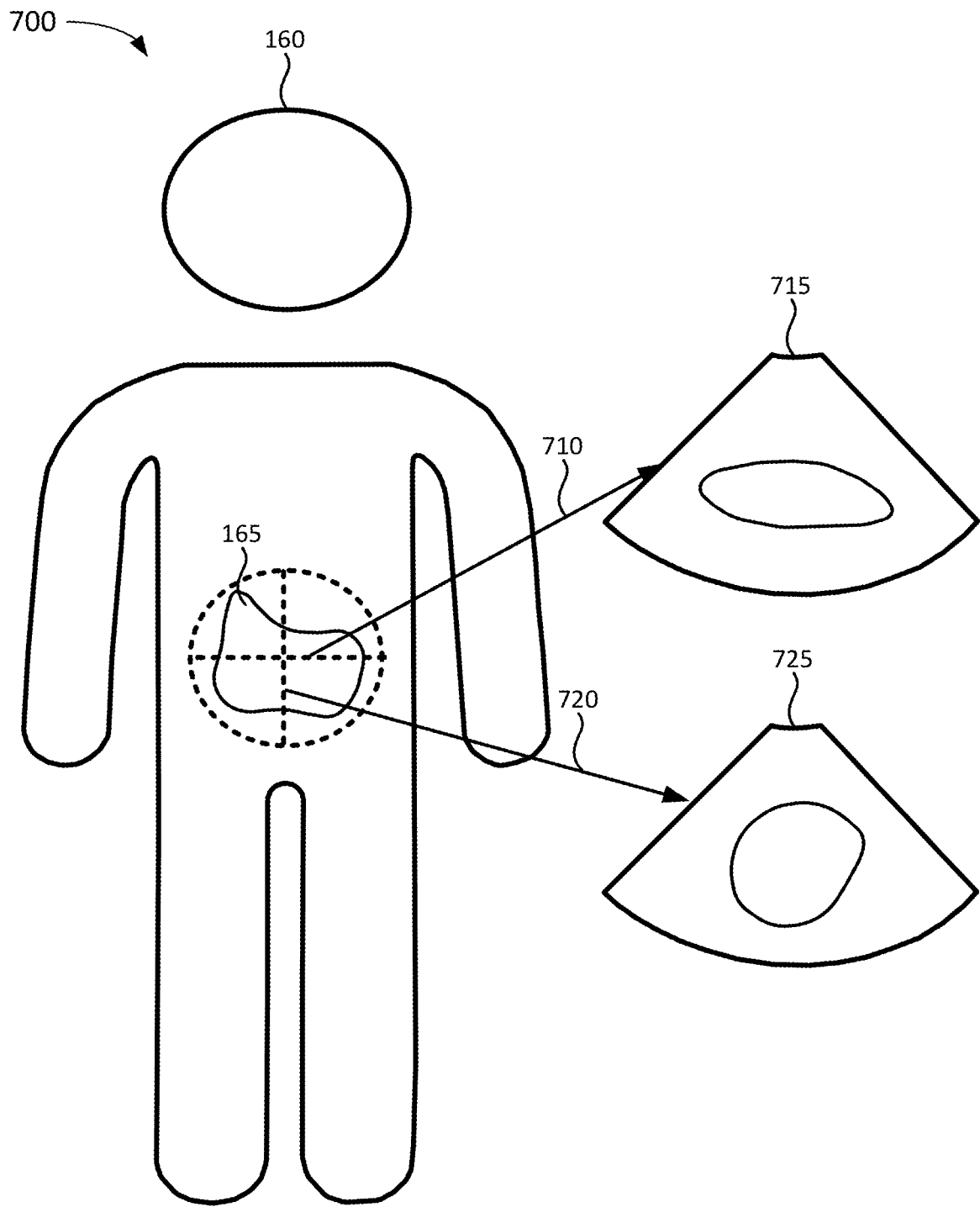
FIG. 7 is a diagram of an exemplary multi-plane visualization according to an implementation described herein.

FIG. 7 is a diagram of an exemplary multi-plane visualization 700 according to an implementation described herein. As shown in FIG. 7, multi-plane visualization 700 may include a scan of patient's 160 organ 165 that includes two aiming mode planes: first aiming mode plane 710 and second aiming mode plane 720. First aiming mode plane 710 may correspond to a transverse plane and second aiming mode plane 720 may correspond to a sagittal plane. First aiming mode plane 710 may be displayed as a first ultrasound image 715 on base unit 120 (not shown in FIG. 7) and second aiming mode plane 720 may be displayed as a second ultrasound image 725 on base unit 120, such as on display 122.

Figure 8:
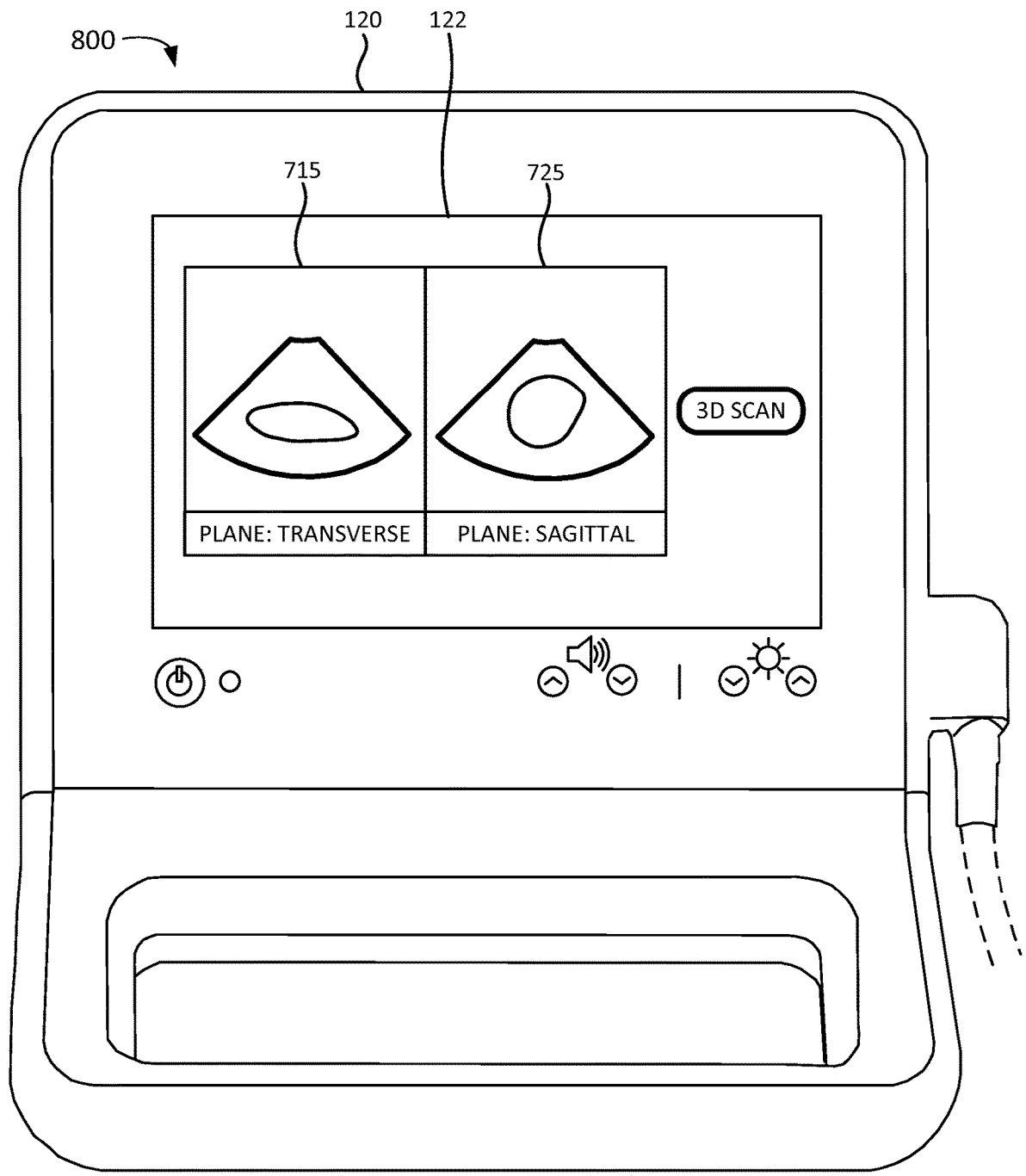
FIG. 8 is a diagram of a first user interface according to an implementation described herein.

FIG. 8 is a diagram of a first user interface 800 according to an implementation described herein. As shown in FIG. 8, in some implementations, first ultrasound image 715 and second ultrasound image 725 may be displayed together on display 122 in real-time or near real-time. Thus, as ultrasound probe 110 scans first aiming mode plane 710, first ultrasound image 715 may be refreshed with a new image. Ultrasound probe 110 may then scan second aiming mode plane 720 and second ultrasound image 725 may be refreshed with a new image.

Figure 9:
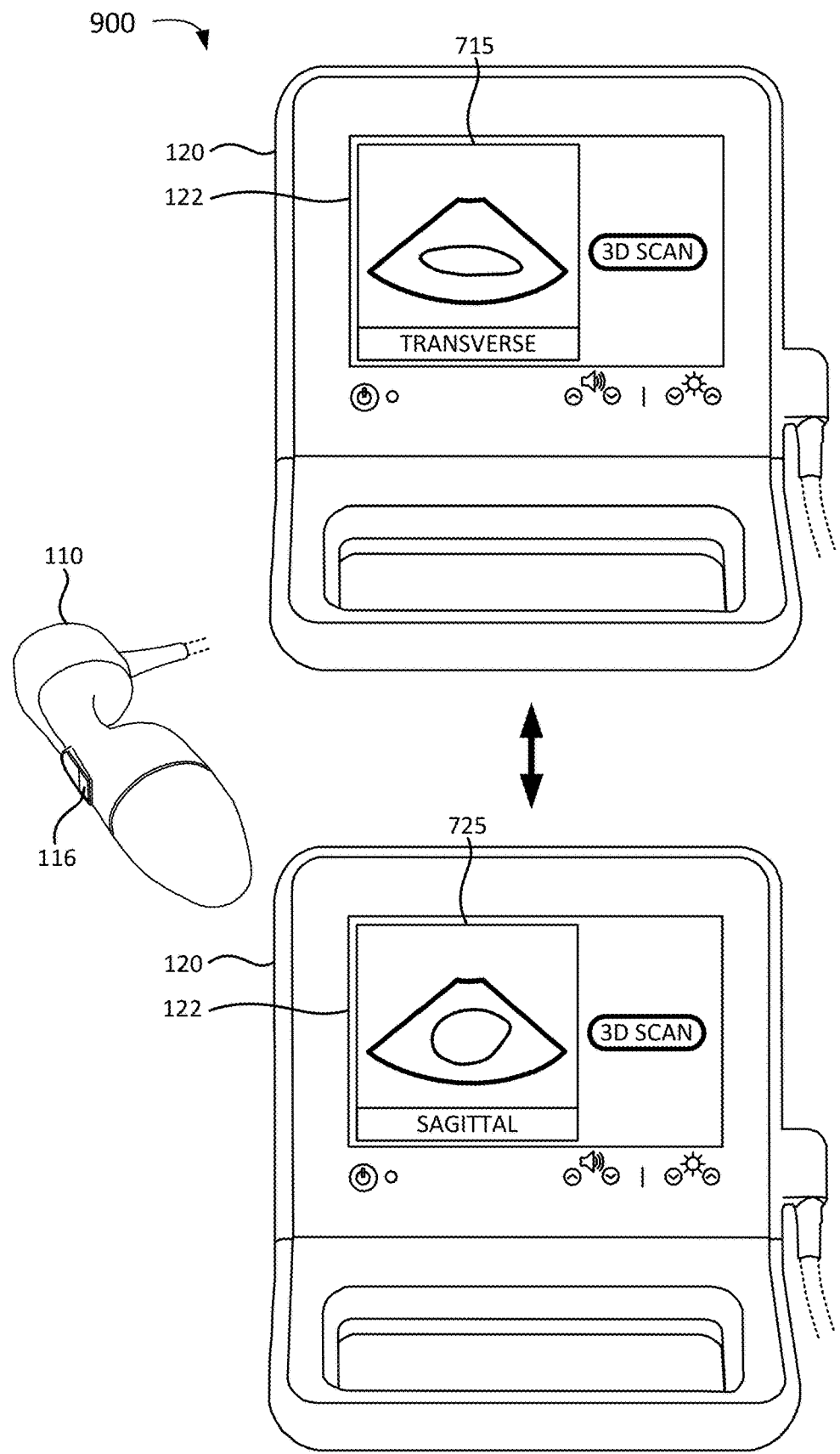
FIG. 9 is a diagram of a second user interface according to an implementation described herein.

FIG. 9 is a diagram of a second user interface 900 according to an implementation described herein. As shown in FIG. 9, in other implementations, display 122 may toggle between first ultrasound image 715 and second ultrasound image 725 at particular intervals or in response to a user pressing toggle switch 116 (and/or another key or button associated with ultrasound system 100). In yet other implementations, first ultrasound image 715 and second ultrasound image 725 may be displayed in a tiled configuration and toggling may change which tile is moved to the front to be viewed by the user.

Figure 10:
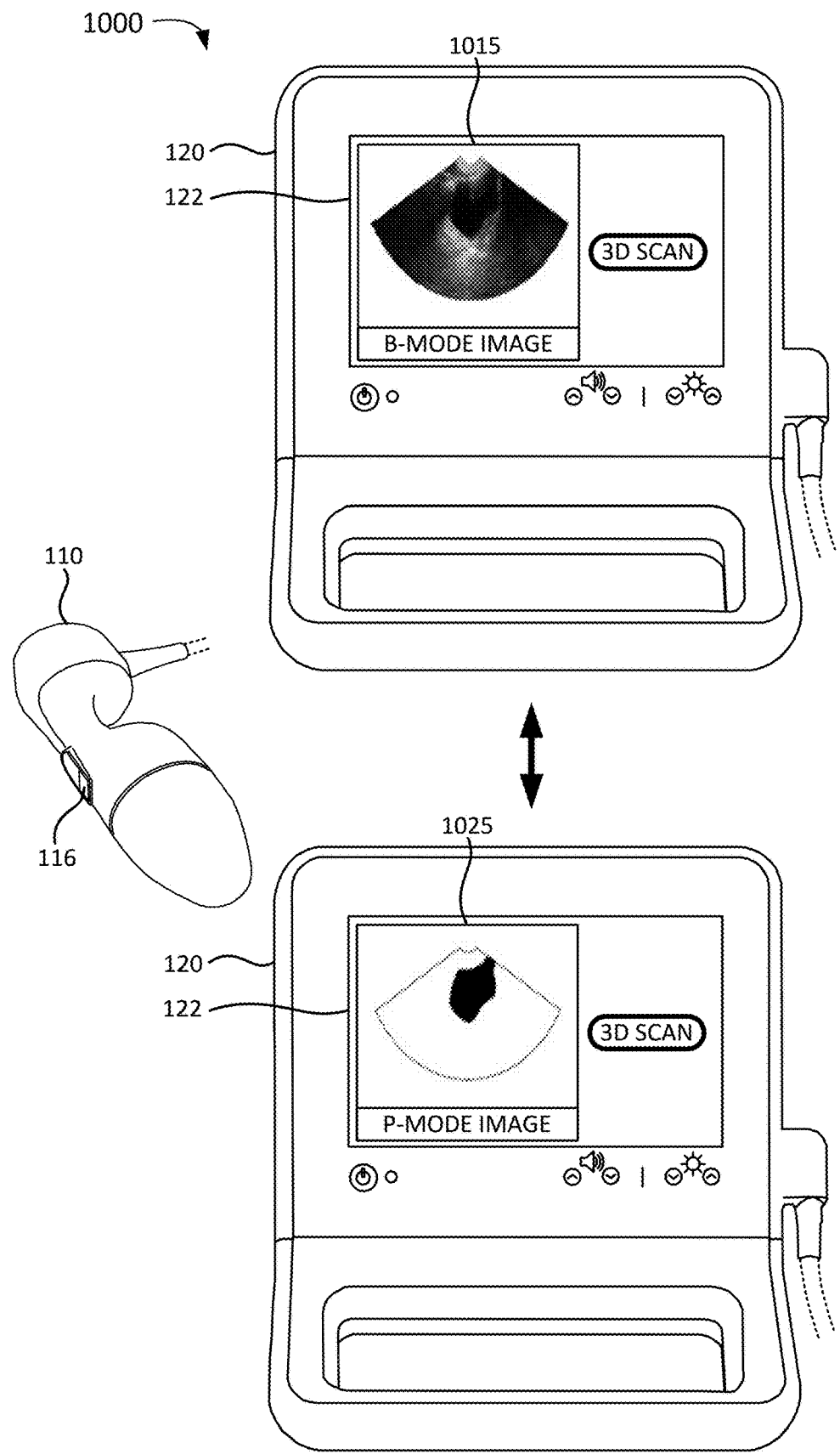
FIG. 10 is a diagram of a third user interface according to an implementation described herein.

FIG. 10 is a diagram of a third user interface 1000 according to an implementation described herein. As shown in FIG. 10, in some implementations, display 122 may toggle between a B-mode ultrasound image 1015 and a P-mode ultrasound image 1025 at particular intervals or in response to a user pressing toggle switch 116 (and/or another key or button associated with ultrasound system 100). In yet other implementations, B-mode ultrasound image 1015 and P-mode ultrasound image 1025 may be displayed in a tiled configuration and toggling may change which tile is moved to the front to be viewed by the user.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while series of blocks have been described with respect to FIGS. 5 and 6, the order of the blocks may be modified in other implementations. Further, non-dependent blocks may be performed in parallel.

Although embodiments described above refer to scanning a bladder, other organs, joints, vessels, and/or body areas, such as an aorta, prostate, kidney, uterus, ovaries, aorta, heart, etc., could scanned and/or imaged in other implementations. Furthermore, in some implementations, obtaining an adequate aiming mode and then proceeding to a 3D scan may be automatic based on a size of an image and/or another parameter.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

The term "logic," as used herein, may refer to a combination of one or more processors configured to execute instructions stored in one or more memory devices, may refer to hardwired circuitry, and/or may refer to a combination thereof. Furthermore, a logic may be included in a single device or may be distributed across multiple, and possibly remote, devices.

For the purposes of describing and defining the present invention, it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A method performed by a computing device, the method comprising:
    selecting, by the computing device, an aiming mode for an ultrasound probe, in response to a selection of the aiming mode made by a user;
    selecting, by the computing device, a first aiming mode plane, scanning mode, or imaging mode;
    selecting, by the computing device, at least one additional aiming mode plane, scanning mode, or imaging mode for the ultrasound probe, wherein the first scanning mode and the at least one additional scanning mode each specify a different number of aiming mode planes to scan, and wherein the first imaging mode and the at least one additional imaging mode each specify a different ultrasound imaging mode;
    toggling, by the computing device, back and forth, or by rotating through, between obtaining and displaying, on a display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe, wherein the toggling is performed until a three-dimensional (3D) scan mode is selected and is performed by:
        activating a single toggle switch or a single toggle selection object, or
        automatically toggling at a particular interval or rate;
    receiving, by the computing device, a selection of the 3D scan mode from the user;
    performing a 3D scan using the ultrasound probe, in response to receiving the selection of the 3D scan mode; and
    displaying one or more ultrasound images generated using the performed 3D scan, or a measurement value generated based on the performed 3D scan, on the display device.

2. The method of claim 1, wherein the ultrasound probe includes a single element ultrasound transducer, a first motor to move the single element ultrasound transducer into different ultrasound imaging planes, and a second motor to move the single element ultrasound transducer along a sector of a particular ultrasound imaging plane.

3. The method of claim 1, wherein the ultrasound probe includes an array of ultrasound transducers and a motor to move the array of ultrasound transducers into different ultrasound imaging planes.

4. The method of claim 1, wherein toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe includes:
    toggling between two orthogonal ultrasound imaging planes.

5. The method of claim 1, wherein toggling between obtaining and displaying, on the display device, ultrasound images associated with the first aiming mode plane, scanning mode, or imaging mode and obtaining and displaying, on the display device, ultrasound images associated with at the least one additional aiming mode plane, scanning mode, or imaging mode using the ultrasound probe includes:
    sequentially rotating between at least three different ultrasound imaging planes.

6. The method of claim 1, wherein toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe includes:
    displaying at least two ultrasound images simultaneously on a display associated with the computing device.

7. The method of claim 1, wherein toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe includes:

displaying a first image associated with the first aiming mode plane, scanning mode, or imaging mode;

detecting activation of the single toggle switch or the single toggle selection object; and switching to displaying another image associated with another aiming mode plane, scanning mode, or imaging mode.

8. The method of claim 1, wherein toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe includes:

automatically toggling, at the particular rate, between a first image, associated with the first aiming mode plane, scanning mode, or imaging mode, and at least one other image, associated with at least one other aiming mode plane, scanning mode, or imaging mode.

9. The method of claim 1, wherein toggling between obtaining and displaying, on the display device, ultrasound images associated with the first aiming mode plane and obtaining and displaying, on the display device, ultrasound images associated with the at least one additional aiming mode plane using the ultrasound probe includes:

controlling a motor to move a single element ultrasound transducer between different ultrasound imaging planes; or controlling an array of ultrasound transducers to generate ultrasound images in different ultrasound imaging planes.

10. A system comprising:
an ultrasound probe; and
a controller unit configured to:
communicate with the ultrasound probe;
select an aiming mode for the ultrasound probe, in response to a user selection of the aiming mode made by a user;
select a first aiming mode plane, scanning mode, or imaging mode for the ultrasound probe;
select at least one additional aiming mode plane, scanning mode, or imaging mode for the ultrasound probe, wherein the first scanning mode and the at least one additional scanning mode each specify a different number of aiming mode planes to scan, and wherein the first imaging mode and the at least one additional imaging mode each specify a different ultrasound imaging mode;
toggle back and forth, or by rotating through, between obtaining and displaying, on a display device, ultrasound images associated with the first aiming mode plane, scanning mode, or imaging mode and obtaining and displaying, on the display device, ultrasound images associated with the at least one additional aiming mode plane, scanning mode, or imaging mode, wherein the toggling is performed until a three-dimensional (3D) scan mode is selected and is performed by:
activating a single toggle switch or a single toggle selection object, or
automatically toggling at a particular interval or rate;

receive a selection of the 3D scan mode from the user;

perform a 3D scan using the ultrasound probe, in response to receiving the selection of the 3D scan mode; and display one or more ultrasound images generated using the performed 3D scan, or a measurement value generated based on the performed 3D scan, on the display device.

11. The system of claim 10, wherein the ultrasound probe includes a single element ultrasound transducer, a first motor to move the single element ultrasound transducer into different ultrasound imaging planes, and a second motor to move the single element ultrasound transducer along a sector of a particular ultrasound imaging plane.

12. The system of claim 10, wherein the ultrasound probe includes an array of ultrasound transducers and a motor to move the array of ultrasound transducers into different ultrasound imaging planes.

13. The system of claim 10, wherein, when toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe, the controller unit is further configured to:

toggle between two orthogonal ultrasound imaging planes.

14. The system of claim 10, wherein, when toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe, the controller unit is further configured to:

sequentially rotate between at least three different ultrasound imaging planes.

15. The system of claim 10, wherein, when toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe, the controller unit is further configured to:

display at least two ultrasound images simultaneously on a screen associated with the controller unit.

16. The system of claim 10, wherein, when toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe, the controller unit is further configured to:

display a first image associated with the first aiming mode plane, scanning mode, or imaging mode;

detect activation of the single toggle switch or the single toggle selection object; and switch to displaying a second image associated with a second aiming mode plane, scanning mode, or imaging mode.

17. The system of claim 10, wherein the ultrasound probe includes a single element ultrasound transducer, and wherein, when toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe, the controller unit is further configured to:
   control a motor to move the single element ultrasound transducer between different ultrasound imaging planes.

18. The system of claim 10, wherein the ultrasound probe includes an array of ultrasound transducers, and wherein, when toggling between obtaining and displaying, on the display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe, the controller unit is further configured to:
   control the array of ultrasound transducers to generate ultrasound images in different ultrasound imaging planes.

19. A device comprising:
   a memory storing instructions; and
   a processor configured to execute the instructions to:
      select an aiming mode for an ultrasound probe, in response to a selection of the aiming mode made by a user;
      select a first aiming mode plane, scanning mode, or imaging mode for the ultrasound probe;
      select at least one additional aiming mode plane, scanning mode, or imaging mode for the ultrasound probe, wherein the first scanning mode and the at least one additional scanning mode each specify a different number of aiming mode planes to scan, and wherein the first imaging mode and the at least one additional imaging mode each specify a different ultrasound imaging mode;
      toggle back and forth, or by rotating through, between obtaining and displaying, on a display device, ultrasound images associated with the first aiming mode plane, scanning mode, or imaging mode and obtaining and displaying, on the display device, ultrasound images associated with the at least one additional aiming mode plane, scanning mode, or imaging mode using the ultrasound probe, wherein the toggling is performed until a three-dimensional (3D) scan mode is selected and is performed by:
         activating a single toggle switch or a single toggle selection object, or
         automatically toggling at a particular interval or rate;
      receive a selection of the 3D scan mode from the user;
      perform a 3D scan using the ultrasound probe, in response to receiving the selection of the 3D scan mode; and
      display one or more ultrasound images generated using the performed 3D scan, or a measurement value generated based on the performed 3D scan, on the display device.

20. The device of claim 19, wherein the ultrasound images include at least one of:
   B-mode ultrasound images;
   Doppler ultrasound images;
   P-mode ultrasound images;
   segmentation map mode ultrasound images;
   harmonic mode ultrasound images; or
   M-mode ultrasound images.

* * * * *